(12) United States Patent
Behrenbruch et al.

(10) Patent No.: US 8,974,232 B2
(45) Date of Patent: Mar. 10, 2015

(54) APPARATUS AND METHOD FOR IMPLEMENTING A MOBILITY AID DEVICE

(75) Inventors: Christian Behrenbruch, Brunswick (AU); William Kaiser, Los Angeles, CA (US); Majid Sarrafzadeh, Anaheim Hills, CA (US); Maxim Batalin, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 567 days.

(21) Appl. No.: 12/920,819

(22) PCT Filed: Mar. 3, 2009

(86) PCT No.: PCT/US2009/035802
§ 371 (c)(1),
(2), (4) Date: Nov. 19, 2010

(87) PCT Pub. No.: WO2009/111427
PCT Pub. Date: Sep. 11, 2009

(65) Prior Publication Data
US 2011/0061697 A1     Mar. 17, 2011

Related U.S. Application Data

(60) Provisional application No. 61/033,710, filed on Mar. 4, 2008.

(51) Int. Cl.
*G09B 19/00* (2006.01)
*A45B 3/00* (2006.01)
*G06F 19/00* (2011.01)

(52) U.S. Cl.
CPC .............. *A45B 3/00* (2013.01); *G06F 19/3481* (2013.01)
USPC ........................... 434/258; 340/573.1; 135/65

(58) Field of Classification Search
USPC ............. 434/258, 247; 135/65, 67; 340/573.1
See application file for complete search history.

(56) References Cited

U.S. PATENT DOCUMENTS

| | | | | |
|---|---|---|---|---|
| 5,511,571 A | * | 4/1996 | Adrezin et al. | 135/66 |
| 5,803,740 A | * | 9/1998 | Gesink et al. | 434/112 |
| 5,853,219 A | * | 12/1998 | Santuccio | 297/5 |
| 6,011,481 A | * | 1/2000 | Luther et al. | 340/686.1 |
| 6,182,058 B1 | | 1/2001 | Kohavi | |
| 6,602,210 B2 | * | 8/2003 | Savet | 600/595 |

(Continued)

FOREIGN PATENT DOCUMENTS

WO     WO2009/111427     9/2009

OTHER PUBLICATIONS

PCT/US2009/035802, Applicant: The Regents of the University of California. International Search Report mailed (Apr. 29, 2009).
PCT/US2009/035802, Applicant: The Regents of the University of California. International Preliminary Report on Patentability (Sep. 7, 2010).
Almeida et al. "Dynamic Fall Detection and Pace Measurement in Walking Sticks." Workshop on High Confidence Medical Devices, Software, and Systems (HCMDSS) Boston, MA, (2007).

(Continued)

*Primary Examiner* — Peter Egloff
(74) *Attorney, Agent, or Firm* — Foley & Lardner LLP; Cliff Z. Liu; Angela D. Murch (57) ABSTRACT

A computer readable storage medium includes executable instructions to receive sensor data measurements associated with usage of a mobility aid device and extract sensor feature parameters from the sensor data measurements. The computer readable storage medium further includes executable instructions to derive a usage state corresponding to the usage of the mobility aid device, based on the sensor feature parameters.

21 Claims, 7 Drawing Sheets

(56) References Cited

U.S. PATENT DOCUMENTS

| | | |
|---|---|---|
| 6,930,603 B2 * | 8/2005 | Jackson ............ 340/539.12 |
| 6,933,855 B2 | 8/2005 | Preston |
| 7,394,385 B2 * | 7/2008 | Franco et al. ............ 340/573.1 |
| 7,914,419 B2 * | 3/2011 | Karkanias et al. ............ 482/8 |
| 7,991,576 B2 * | 8/2011 | Roumeliotis ............ 702/159 |
| 2003/0089389 A1 * | 5/2003 | Meador ............ 135/65 |
| 2005/0067816 A1 * | 3/2005 | Buckman ............ 280/730.1 |
| 2006/0025229 A1 | 2/2006 | Mahajan et al. |
| 2006/0070646 A1 * | 4/2006 | Denman ............ 135/66 |
| 2006/0129308 A1 | 6/2006 | Kates |
| 2006/0282021 A1 | 12/2006 | DeVaul et al. |
| 2008/0139899 A1 * | 6/2008 | Student et al. ............ 600/301 |

OTHER PUBLICATIONS

Bateni et al., "Assistive devices for balance and mobility: benefits, demands, and adverse consequences." Arch Phys Med Rehab, vol. 86, pp. 134-145 (2005).

Hester, et al., "Using Wearable Sensors to Analyze the Quality of Use of Mobility Assistive Devices," Proc. Intl. Workshop on Wearable and Implantable Body Sensor Networks (2006).

Kannus et al., "Fall-induced injuries and deaths among older adults." JAMA 28:20, pp. 1895-1899 (1999).

Wu et al., "The SmartCane system: an assistive device for geriatrics." Proc. ICST $3^{rd}$ Int'l Conf. on Body Area Networks (Mar. 13-15, 2008).

PCT/US2009/035802. Int'l Search Report dated Apr. 29, 2009.

* cited by examiner

FIG. 7

APPARATUS AND METHOD FOR IMPLEMENTING A MOBILITY AID DEVICE

CROSS-REFERENCE TO RELATED APPLICATION

This application is a National Stage Entry of PCT/US2009/035802, filed Mar. 3, 2009, which claims the benefit of U.S. Provisional Patent Application Ser. No. 61/033,710, filed Mar. 4, 2008, entitled, "Smart Assistive Devices", the contents of which are incorporated herein by reference.

STATEMENT REGARDING FEDERALLY SPONSORED RESEARCH OR DEVELOPMENT

This invention was made with Government support under ANI0331481, awarded by the National Science Foundation. The Government has certain rights in the invention.

FIELD OF THE INVENTION

The invention relates generally to assistive devices and more particularly to an apparatus and method for implementing a mobility aid device.

BACKGROUND

Falls are known to be particularly serious among the elderly and disabled. The number of elderly individuals with fall-induced injuries is increasing significantly. A wide range of disabilities and environmental risks specifically contribute to the risk of falling, and the disability of age-related cognitive impairments nearly doubles the risk of falling.

Conventional assistive devices such as canes have been used to reduce the risk of falling by providing physical support and supplementary sensing feedback to users. These devices typically provide a sensory input for the user that may contribute to maintaining stability. However, the use of these conventional assistive devices introduces an additional cognitive burden to users who suffer from cognitive disability due to age or other factors. For example, falls caused by the improper usage of the cane are particularly acute in the elderly and disabled where reduced cognitive capacity accompanied by the burden of managing cane motion leads to increased risks. In addition, abandonment of the cane, disorders and disability resulting from repetitive stress, usage of the cane in the presence of environmental hazards including obstacles, stairs, and surfaces with uncertain support and friction and disruption of balance due to the competition of attention between cane manipulation and mobility also contribute to the potential risk of falling.

It would therefore be desirable to develop a mobility aid device that performs real-time monitoring of activities related to usage of the mobility aid device. In addition, it would be desirable to develop a mobility aid device that provides real-time feedback and active guidance regarding proper usage of the mobility aid device to a user.

SUMMARY

Embodiments of the invention relate to an apparatus and method for implementing a mobility aid device. In one embodiment, a computer readable storage medium includes executable instructions to receive sensor data measurements associated with usage of a mobility aid device and extract sensor feature parameters from the sensor data measurements. The computer readable storage medium further includes executable instructions to derive a usage state corresponding to the usage of the mobility aid device, based on the sensor feature parameters.

In a second embodiment, a mobility aid device is disclosed. The mobility aid device includes sensors and a computational unit coupled to the sensors. The sensors are configured to acquire sensor data measurements associated with usage of the mobility aid device. The computational unit is configured to extract sensor feature parameters from the sensor data measurements. The computational unit is further configured to derive a usage state corresponding to the usage of the mobility aid device, based on the sensor feature parameters.

In a third embodiment, a mobility aid device is disclosed. The mobility aid device includes sensors. The sensors include a three-axis accelerometer, a single-axis gyroscope and pressure sensors configured to detect an applied force, a linear acceleration and an angular rate associated with usage of the mobility aid device. The mobility aid also includes a computational unit coupled to the sensors. The computational unit is configured to process outputs of the sensors to provide feedback regarding the usage of the mobility aid device.

BRIEF DESCRIPTION OF THE FIGURES

Embodiments of the invention are more fully appreciated in connection with the following detailed description taken in conjunction with the accompanying drawings, in which.

Like reference numerals refer to corresponding parts throughout the several views of the drawings.

DETAILED DESCRIPTION

Figure 1:
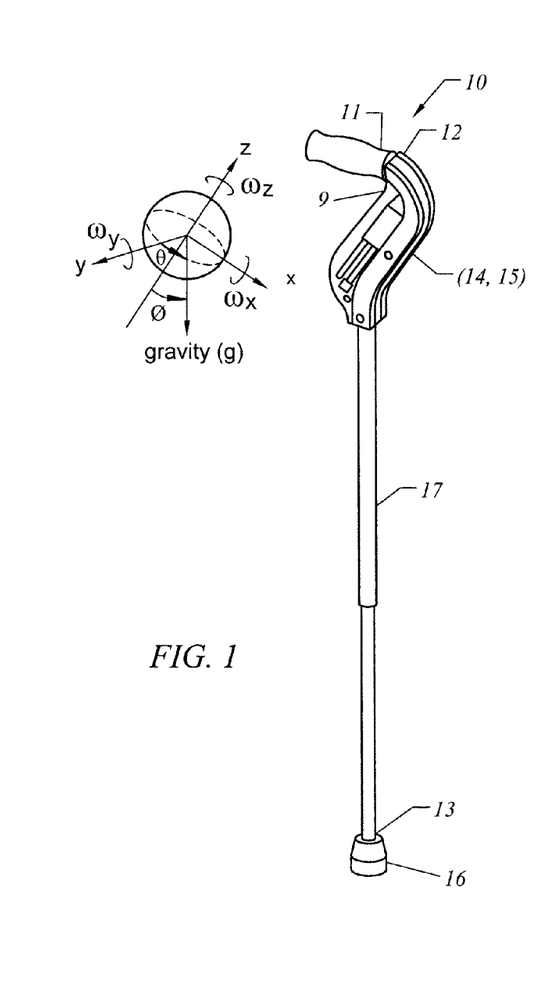
FIG. 1 illustrates an exemplary architecture of a mobility aid device in accordance with one embodiment of the present invention.
Figure 2A:
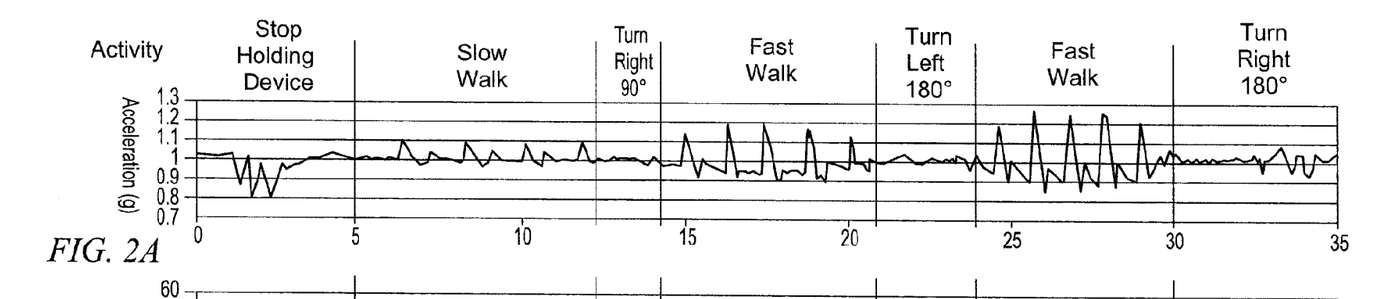
FIGS. 2*a*-2*h* illustrate sensor data measurements acquired during a typical usage of the mobility aid device shown in FIG. 1, in accordance with one embodiment of the present invention.
Figure 2B:
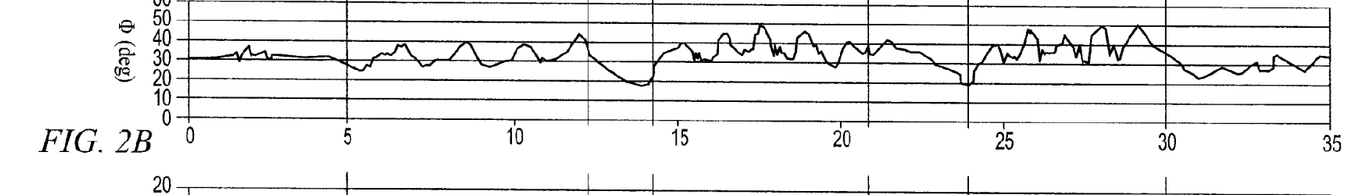
Figures 2C, 2D:
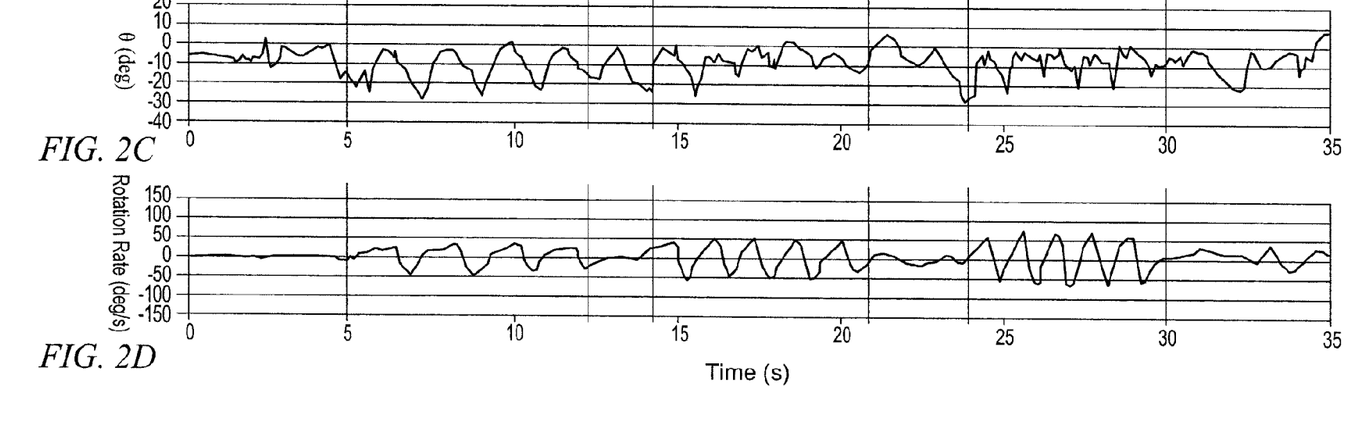
Figure 2E:
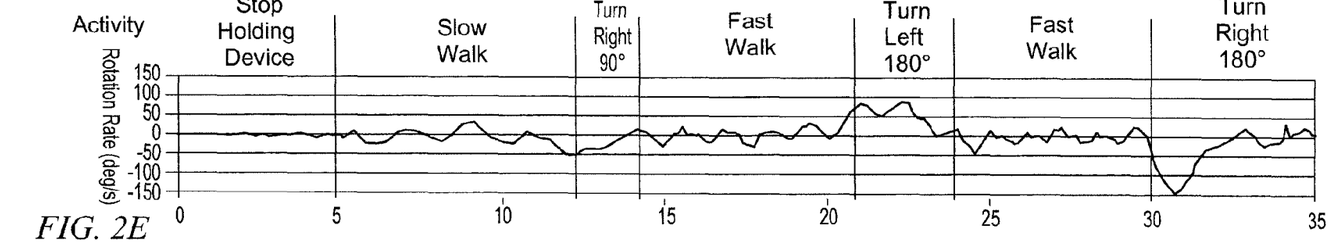
Figure 2F:
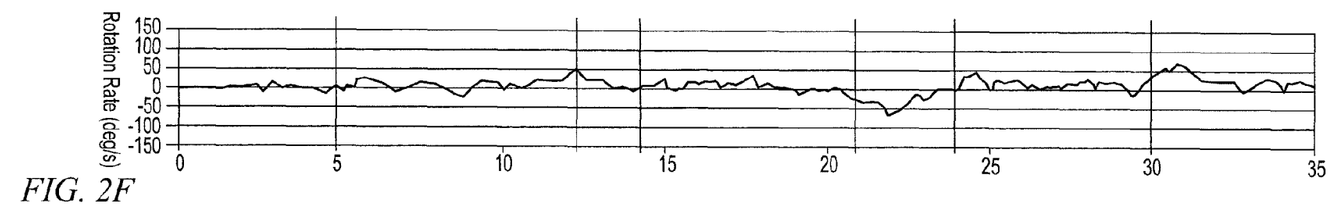
Figure 2G:
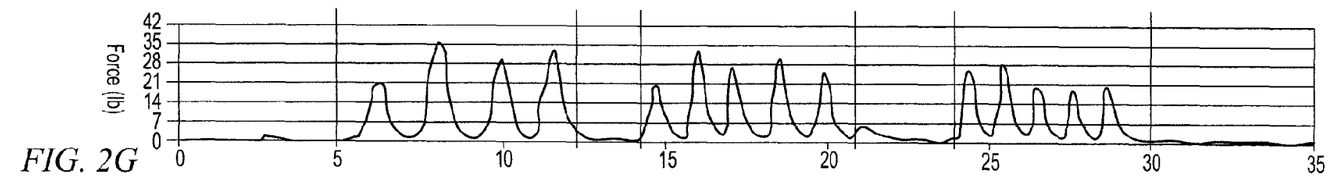
Figure 2H:
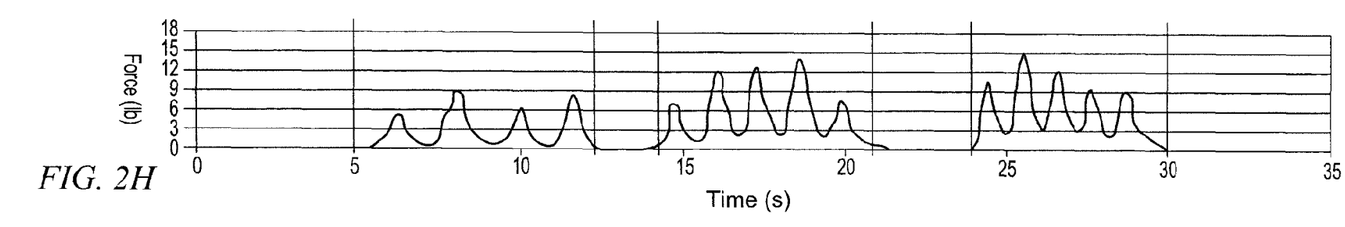

FIG. 1 illustrates an exemplary architecture of a mobility aid device 10 in accordance with one embodiment of the present invention. In one embodiment, the mobility aid device 10 includes a handle 11 at one end and a tip 13 at another end. Between the handle 11 and the tip 13 is an elongated case 17 that terminates at the tip 13. The mobility aid device 10 also includes a plurality of sensors configured to acquire data measurements during usage of the mobility aid device 10. The plurality of sensors may include one or more wireless sensors including a three-axis accelerometer 14, three single-axis gyroscopes 15 and two contact pressure sensors 12, 16. In a particular implementation, the three single-axis gyroscopes 15 are mounted perpendicularly and enclosed in a case 9 near the handle 11 of the mobility aid device 10 along with the three-axis accelerometer 14. The contact pressure sensor 16 is configured to detect the downward force at the tip 13 of the mobility aid device 10 while the contact pressure sensor 12 is configured to detect the force corresponding to a user's grip at the handle 11 of the mobility aid device 10. The accelerometer 14 and the gyroscopes 15 are configured to detect the linear acceleration and angular rate of the mobility aid device 10 due to the forces exerted by a user of the mobility aid device 10. The mobility aid device 10 also includes a wireless interface (not shown in FIG. 1) that enables the acquisition and processing of a diverse set of sensor signals by integrating the plurality of sensors 12, 14, 15, 16 with wearable sensors, standard handheld devices, the Internet and remote services such as call centers and medical enterprises.

In one embodiment, the data measurements acquired from the plurality of sensors 12, 14, 15 and 16 are processed by a computational unit (not shown in FIG. 1) integrated into the mobility aid device 10. A low-pass filter may be used to remove noise from the data measurements. In one embodiment, in order to minimize the volume of data measurements resulting from the processing of the sensor signals, the case 9 of the mobility aid device 10 is configured to follow the contour of the mobility aid device 10. As a result, in one implementation, the reference coordinate system of the mobility aid device 10 forms a 30° angle with respect to the gravity. As illustrated, in one embodiment, the mobility aid device 10 represents a cane. The mobility aid device 10 may also be implemented as walkers, wheelchairs or rollators in other embodiments.

FIGS. 2a-2h illustrate sensor data measurements acquired during a typical usage of the mobility aid device 10 shown in FIG. 1, in accordance with one embodiment of the present invention. In one embodiment, the sensor data measurements are represented as a time-series of data measurements pertaining to various activities performed by a user of the mobility aid device 10, such as, for example, "Stop Holding device", "Slow Walk", "Turn Right 90°", "Fast Walk", "Turn Left 180°" and "Turn Right 180°". In particular, the time-series of data measurements represent motion, rotation, force, strain and impact signals relating to the orientation of the mobility aid device 10 with respect to gravity and swing characteristics associated with the mobility aid device 10.

FIG. 2-a illustrates a time-series of sensor data measurements representing the magnitude of the resultant acceleration vector on the mobility aid device 10. In one embodiment, the resultant acceleration vector includes the acceleration caused by gravity g and the acceleration caused by external forces on the mobility aid device 10. The magnitude and periodicity typically correspond with the intensity of a "walking motion" associated with the user.

FIG. 2-b illustrates a time-series of sensor data measurements contributing to the resultant acceleration vector defined by a tilt angle $\phi$ with respect to the z-axis. FIG. 2-c illustrates a time-series of sensor data measurements contributing to the resultant acceleration vector defined by a tilt angle $\theta$ with respect to the x-axis. Since the reference coordinate system of the mobility aid device 10 is tilted at 30 degrees, in one embodiment, the tilt angle $\phi$ fluctuates around the 30-degree mark. The tilt angle $\theta$ illustrates that the mobility aid device 10 is tilted to one side (towards or away from the user) while walking. In this case, $\theta$ is consistently in the negative range (leaning left), which typically represents a user holding the mobility aid device 10 on the right.

FIG. 2-d illustrates a time-series of sensor data measurements representing swing characteristics generated during usage of the mobility aid device 10. In one embodiment, the swing characteristics are defined by the pitch angular velocity, $\omega_y$. Note that the rate of change of the tilt angle in FIG. 2-d corresponds to the slope of the tilt angle $\phi$ illustrated in FIG. 2-b.

FIG. 2-e and FIG. 2-f illustrate a time-series of sensor data measurements representing the angular velocity resulting from a user's change in direction. The yaw ($\omega_z$) and roll ($\omega_x$) gyroscopes detect the user's change of direction due to the fact that the reference coordinate system on the mobility aid device 10 is tilted.

FIG. 2-g illustrates a time-series of sensor data measurements representing the magnitude of the contact forces at the tip 13 of the mobility aid device 10. In one embodiment, the pressure sensor 16 is used to detect the magnitude of the contact forces at the tip 13 of the mobility aid device 10. FIG. 2-h illustrates a time-series of sensor data measurements representing the magnitude of the contact forces at the handle 11 of the mobility aid device 10. In one embodiment, the pressure sensor 12 is used to detect the magnitude of the contact forces at the handle 11 of the mobility aid device 10.

Figure 3:
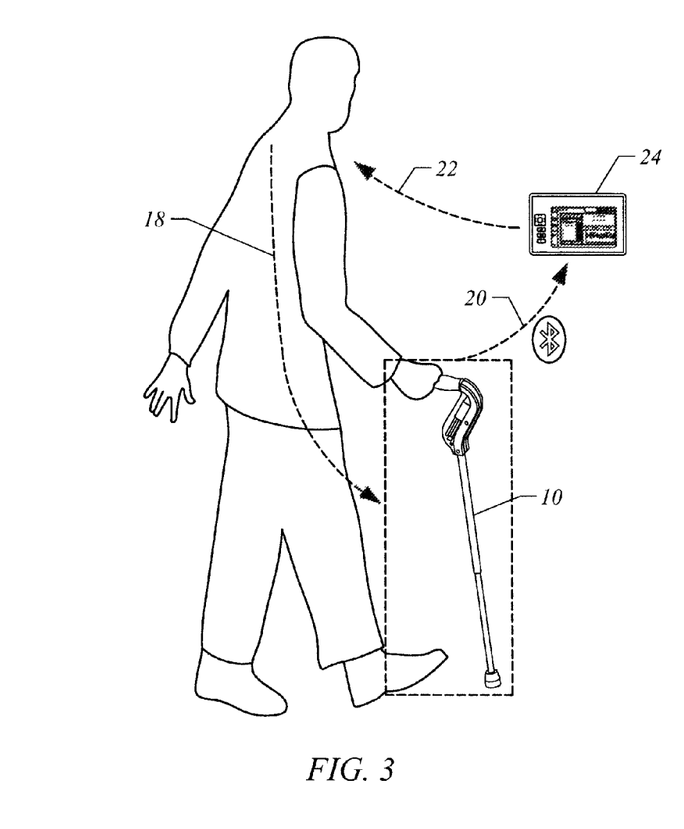
FIG. 3 illustrates an exemplary set of operations performed by the mobility aid device shown in FIG. 1, in accordance with one embodiment of the present invention.

FIG. 3 illustrates an exemplary set of operations performed by the mobility aid device 10 shown in FIG. 1, in accordance with one embodiment of the present invention. In a first operation 18, the mobility aid device 10 captures data measurements associated with usage of the mobility aid device 10 in real-time, through one or more of the sensors 12, 14, 15 and 16. In a second operation 20, the sensor data measurements are processed locally by software modules in the computational unit in the mobility aid device 10. In an alternate embodiment, the unprocessed sensor data measurements may also be streamed to a personal device 24 via the wireless interface on the mobility aid device 10 and processed using software modules in the personal device 24. The wireless interface may include, for example, a low power Bluetooth radio interface. The personal device 24 may include, for example, a cell phone, a Personal Digital Assistant (PDA) or a laptop/desktop computer.

In a third operation 22, the software modules analyze the sensor data measurements and provide real-time feedback indicating information about usage of the mobility aid device 10. Specifically, and as will be discussed in greater detail below, the software modules include a sensor processing and inference module that analyzes the sensor data measurements and provides accurate state information about a usage state associated with usage of the mobility aid device 10 in real-time. In particular, the sensor processing and inference module classifies an action performed by the user into a usage state associated with the mobility aid device 10 and provides feedback on the usage of the mobility aid device 10 to the user. The user then adjusts his or her current movements by applying an appropriate action in accordance with the feedback suggested by the mobility aid device 10. The action performed by the user is again classified into a usage state and the feedback cycle is repeated until the sensor processing and inference module detects proper usage of the mobility aid device 10.

In one embodiment, the feedback on the usage of the mobility aid device 10 is accomplished via an audio interface module in the computational unit in the mobility aid device 10. In a particular embodiment, the audio interface module may be coupled to a piezoelectric speaker embedded in the mobility aid device 10. The piezoelectric speaker may be configured to generate audio tones corresponding to various usage states associated with the mobility aid device 10.

Figure 4:
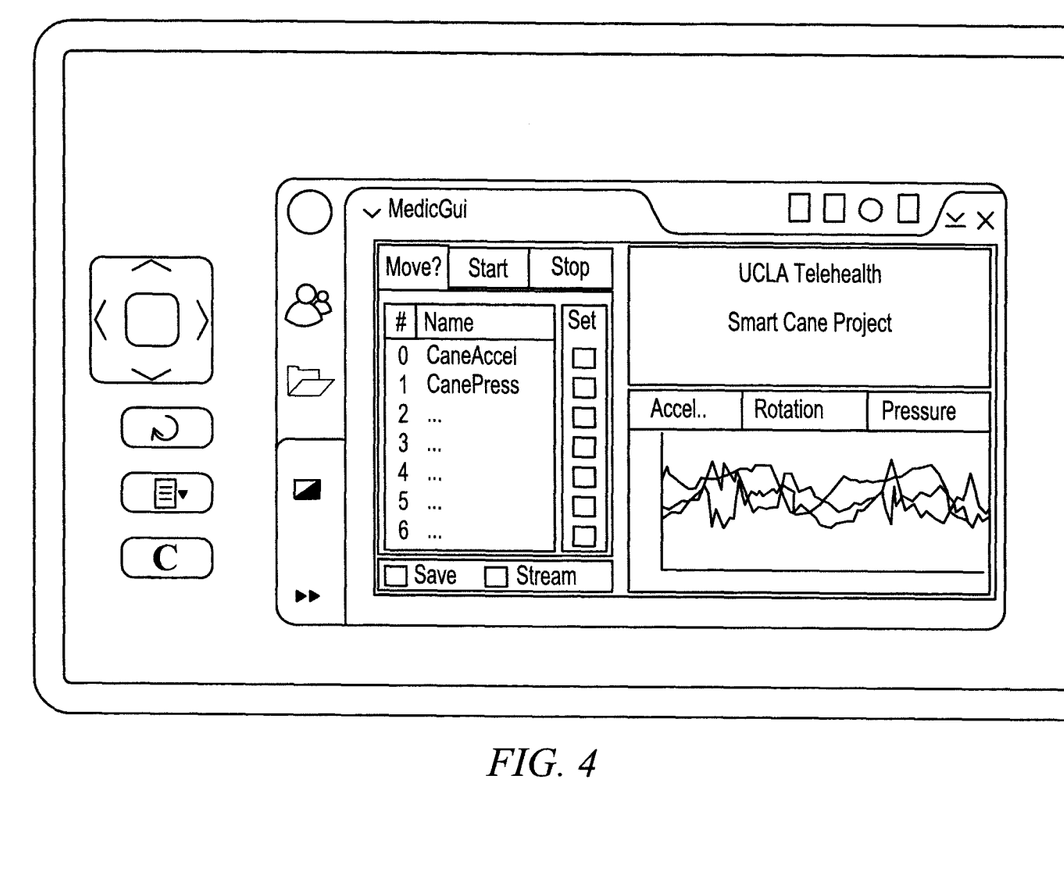
FIG. 4 illustrates an exemplary graphical user interface (GUI) screen on a personal device, in accordance with one embodiment of the present invention.

Accordingly, the audio tones can be used to provide active guidance to a user using the mobility aid device 10. In another embodiment, the feedback on the usage of the mobility aid device 10 is accomplished via a graphical user interface (GUI) screen on the personal device 24. In one embodiment, the GUI generates an audio output and a visual output corresponding to a usage state associated with the mobility aid device 10. FIG. 4 illustrates an exemplary graphical user interface (GUI) screen on the personal device 24, in accordance with one embodiment of the present invention. As illustrated, the raw sensor signals and the signal processing and inference output may also be viewed on the GUI in real-time.

Figure 5:
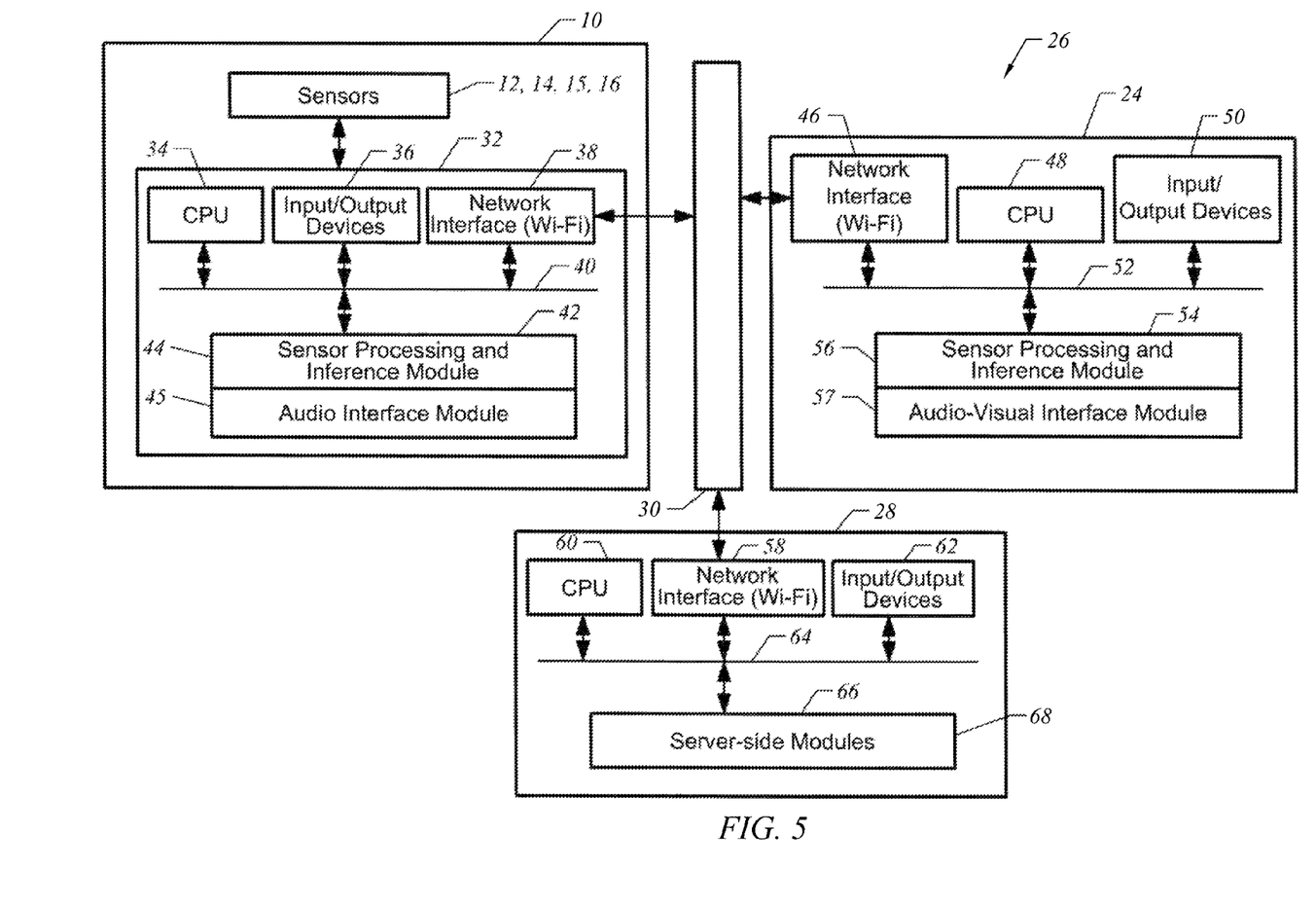
FIG. 5 illustrates an exemplary network for operating the mobility aid device shown in FIG. 1, in accordance with one embodiment of the present invention.

FIG. 5 illustrates an exemplary network 26 for operating the mobility aid device 10 shown in FIG. 1, in accordance with one embodiment of the present invention. The network 26 includes the mobility aid device 10 connected to the personal digital assistant 24 and a centralized server 28 via a communication channel 30, which may be any wired or wireless communication channel. As mentioned above, the mobility aid device 10 includes a plurality of sensors 12, 14, 15 and 16 configured to acquire a plurality of sensor data measurements associated with usage of the mobility aid device 10. The mobility aid device 10 further includes a computational unit 32 coupled to the plurality of sensors 12, 14, 15 and 16. The computational unit 32 includes various components, such as a central processing unit 34, input/output devices 36 and a network interface 38, which are linked by a bus 40. The network interface 38 provides connectivity to the communication channel 30, thereby allowing the mobility aid device 10 to operate in a networked environment. A sensor processing and inference module 44 and an audio interface module 45 are stored in a memory 42, which is connected to the bus 40. The sensor processing and inference module 44 includes executable instructions to extract a plurality of sensor feature parameters from the sensor data measurements and derive a usage state corresponding to the usage of the mobility aid guidance device, based on the sensor feature parameters. The audio interface module 45 includes executable instructions to relay an audio output of the usage state of the mobility aid device 10, in real-time, to a user. The audio interface module 45 further includes executable instructions to generate a plurality of audio tones corresponding to various usage states associated with the mobility aid device 10.

The Personal Digital Assistant 24 similarly includes various components, such as a network interface 46, a central processing unit 48 and input/output devices 50, which are linked by a bus 52. A sensor processing and inference module 56 is stored in a memory 54 connected to the bus 52. The sensor processing and inference module 56 includes executable instructions to extract a plurality of sensor feature parameters from the sensor data measurements and derive a usage state corresponding to the usage of the mobility aid guidance device, based on the sensor feature parameters. The audio-visual interface module 57 includes executable instructions to relay an audio output and a visual output of the usage state of the mobility aid device 10, in real-time, to a user.

The centralized server 28 also includes various components, such as a network interface 58, a central processing unit 60 and input/output devices 62, which are linked by a bus 64. A plurality of server-side modules 68 are stored in a memory 66 connected to the bus 64. The server-side modules 68 include executable instructions to store the usage state associated with a plurality of users. The server-side modules 68 further include executable instructions to analyze the usage state and predict a fall risk factor associated with each user. The server-side modules 68 may also include executable instructions to communicate the fall risk factor to each user or to a caregiver associated with each of the users, based on the analysis.

It should be noted that the network interfaces 38, 46 and 58 may be implemented as wired or wireless interfaces. It should also be noted that the executable modules stored in memory units 42, 54 and 66 are exemplary. Additional modules, such as an operating system module or GUI module may also be included. It should be appreciated that the functions of the modules may be combined. In addition, the functions of the modules may be distributed across the network 26 in any number of ways.

In an exemplary set of operations, the sensor processing and inference module 44 in the computational unit 32 in the mobility device 10 processes and analyzes the sensor data measurements received from the plurality of sensors 12, 14, 15 and 16. In an alternate embodiment, and as discussed above, the unprocessed sensor data measurements may also be streamed to the personal device 24 via the network interface 38 on the mobility device 10 and processed and analyzed using the sensor processing and inference module 56 in the personal device 24. In certain embodiments, the processed sensor data measurements from either the mobility aid device 10 or the personal device 24 may also be sent via the communication channel 30 to the centralized server 28 for further development, verification, and optimization.

As discussed above, the sensor processing and inference module 44 or 56 is configured to analyze the sensor data measurements and provide accurate state information regarding a user's usage of the mobility aid device 10, in real-time, to a user. In a particular embodiment, the sensor processing and inference module 44 or 56 is configured to extract a plurality of sensor feature parameters from the sensor data measurements and derive a usage state corresponding to the usage of the mobility aid guidance device, based on the sensor feature parameters. The functions performed by sensor processing and inference module 44 or 56 are discussed in greater detail below.

In a particular implementation, the sensor processing and inference module 44 or 56 processes the time-series of data measurements acquired from the plurality of sensors 12, 14, 15 and 16 to extract one or more sensor feature parameters. In one embodiment, the sensor feature parameters include a fundamental frequency amplitude parameter and spectrum energy parameter. In a particular embodiment, a Fast Fourier Transform (FFT) technique is used to extract the sensor feature parameters. Equation (1) illustrates a fundamental frequency parameter ($f_{amp}$) extracted from a discrete time-series of sensor data measurements x(t). Equation (2) illustrates a spectrum energy parameter ($f_{energy}$) extracted from a discrete time-series of sensor data measurements x(t). Note that X(k) =FFT(x(t)), and N represents the length of the Fast Fourier Transform (FFT) vector.

$$f_{amp} = \max_k \|X(k)\| \quad (1)$$

$$f_{energy} = \sum_{k=1}^{N/2} X(k) * X(k) \quad (2)$$

The sensor processing and inference module 44 or 56 may also be configured to extract additional sensor feature parameters, such as, for example, a fundamental frequency parameter, $f_{ind}=\arg \max_k \|X(k)\|$, the ratio of the fundamental frequency amplitude parameter to the spectrum energy parameter $f_{ratio}=f_{amp}/f_{energy}$, and time features related to transient usage states such as, for example, the mean of a time-series of sensor data measurements x(n), $$f_{avg} = \sum_{n=1}^{N} x(n)/N,$$

the maximum value of a time-series of sensor data measurements x(n), $f_{max}=\max_n x(n)$ and the maximum slope of a time-series of sensor data measurements x(n), $f_{der\ max}=\max_n d/dx x(n)$. In one embodiment, the extracted sensor feature parameters are represented as a sensor feature vector $F=\{F_1 \ldots, F_n\}$.

The sensor processing and inference module 44 or 56 then derives a usage state corresponding to the usage of the mobility aid guidance device based on the sensor feature parameters. In one embodiment, the typical usage states derived by the sensor processing and inference module 44 or 56 may include, for example, a "Proper Use" state, an "Improper Use" state and a "Not Used" state.

In a particular embodiment, a Naïve Bayes classifier model is used to infer a usage state C based on the derived sensor feature vector F. Specifically, the Naïve Bayes classifier model is used to infer the probability of a user being in one of the states C based on the sensor feature vector F, as follows.

If the usage state C is known and each feature $F_i$ is conditionally independent of every other feature $F_j$ wherein j≠i, the conditional probability of the feature vector given a usage state may be expressed as a product of the conditional probabilities of each sensor feature parameter given the usage state.

In other words, $$p(F|C) = \prod_{i=1}^{n} p(F_i|C).$$

Likewise, the marginal probability of the feature vector may be expressed a product of the prior marginal probabilities of each feature, i.e., $$p(F) = \prod_{i=1}^{n} p(F_i).$$

In one embodiment, the conditional distribution of the usage states may be expressed as shown in equation (3) below.

$$p(C|F) = \frac{p(C)\prod_{i=1}^{n} p(F_i|C)}{\prod_{i=1}^{n} p(F_i)} \quad (3)$$

In certain embodiments, the Naïve Bayes classifier model may also be trained offline based on a known dataset of usage states. In one embodiment, the training process may be implemented as a supervised training process that maps input feature vectors into a plurality of output classes by analyzing a plurality of input-output examples in the classifier.

In a particular embodiment, the training process includes a feature extraction operation, a Gaussian Cluster Discretization operation and a Maximum Likelihood Estimation operation. As will be discussed in greater detail below, the training data used in the training process may be used to determine the number of discrete attributes required in each feature parameter in the Naïve Bayes classifier and the likelihood of occurrence of the feature parameters.

The feature extraction operation in the training process is similar to the feature extraction performed by the sensor processing and inference module 44 or 56 discussed above. The amplitude of the fundamental frequency component $f_{amp}$ (equation 1) and spectral energy $f_{energy}$ (equation 2) are extracted as sensor feature parameters.

The sensor feature parameters extracted from the training data in the feature extraction step are then clustered into a discrete feature space to learn the parameters of the Naïve Bayes classifier in linear time. As will be appreciated by those skilled in the art, the process of discretization improves the performance of the Naïve Bayes classifier. Since a priori knowledge of the feature distribution in the training data set is unknown, in one embodiment, a Gaussian (normal) probability distribution is assumed in order to maximize the information entropy and allow model-free clustering without requiring an explicit underlying domain model. Accordingly, in one embodiment, a Gaussian clustering technique is used to cluster the sensor feature parameters into a discrete feature space. In a first operation, the mean (μ) and standard deviation (σ) values representing the Gaussian clusters of the data points in the various supervised training samples are extracted for each feature parameter associated with each of the sensors 12, 14, 15 and 16. In a second operation, the Gaussian clusters are used to transform the continuous data space of each feature parameter into discrete states. The continuous data space of each feature F may be described by C Gaussian probability distributions ($G(F)=\{G_c(F)\}, \forall c \in \{1, \ldots, C\}$), corresponding to each supervised training sample, c. A set of discrete intervals I are formed from the continuous probability distributions G(F) with each interval $i_j \in (u_j, v_j)$, where $u_j$ and $v_j$ are the lower and upper boundary values, respectively. An interval boundary between $v_j$ and $u_{j+1}$ is typically formed at $v_j$ only when the following conditions are met as shown in equation (4) and equation (5) below:

$$v_j > G_c(F; \mu_c + \delta, \sigma_c) \quad (4)$$

$$v_j < \forall_{c'=c+1}^{C} G_{c'}(F; \mu_{c'} - \delta, \sigma_{c'}) \quad (5)$$

Note that $\mu_c < \mu_{c'}$, since the Gaussian distributions are pre-sorted based on their mean values, and δ is a threshold number based on σ. The feature values F from the original continuous space are mapped to the discrete intervals $i_j$ and all relevant probabilities are estimated with respect to $i_j$.

Once the data space of the input feature vector is discretized as discussed above, in a third operation, a maximum likelihood model is constructed. The conditional likelihood term in the Bayes classifier (computed in equation 3) can be trained through a supervised learning process by manually assigning the class labels in the training process, which associate the input feature vectors with a given class in the Naïve Bayes classifier as shown in equation (6) below:

$$p(F_i = f_i | C = c) = \frac{\text{count}(F_i = f_i \wedge C = c)}{\text{count}(C = c)} \quad (6)$$

Therefore, as a result of the training process described above, a Naïve Bayes model that correlates sensor feature parameters with different usage states can be developed.

Figure 6:
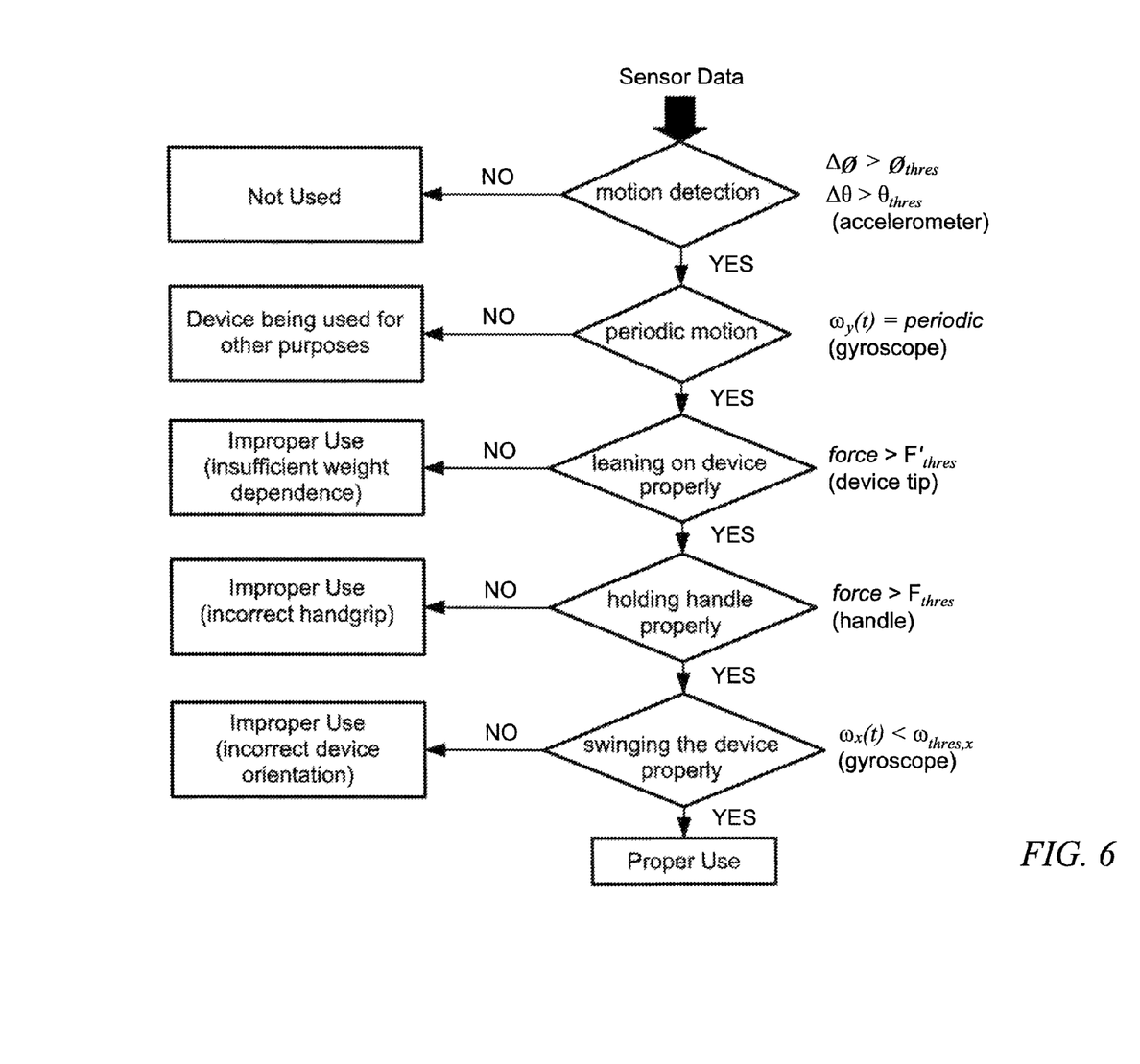
FIG. 6 illustrates an exemplary decision tree-based classification technique, in accordance with one embodiment of the present invention.

In another embodiment, a decision tree-based classification technique may be used to classify sensor data measurements into one or more of the usage states, "Proper Use", "Improper Use" and "Not Used". FIG. 6 illustrates an exemplary decision tree-based classification technique, in accordance with one embodiment of the present invention. In one embodiment, the usage states are derived based on computing threshold values based on the sensor data measurements. The threshold values are used to classify, in real-time, a particular usage state corresponding to a user of the mobility aid device 10, as follows.

Initially, motion data measurements acquired from an accelerometer 14 (shown in FIG. 1) are analyzed. If the motion data measurements do not satisfy the threshold conditions associated with "motion detection" in the mobility aid device 10, then the mobility aid device 10 is classified into a "Not Used" state. In the illustrated example, if the changes in the tilt angles θ and φ do not exceed the threshold values set for θ and φ, then the mobility aid device 10 is classified into a "Not Used" state. If, however, the motion data measurements satisfy the threshold conditions, then the classification process proceeds to the next operation, wherein "periodic motion" measurements from a gyroscope 15 (shown in FIG. 1) are used to determine if the mobility aid device 10 satisfies a "Device being used for other purposes" classification state. Observe that a decision is made at each operation in the classification technique through threshold detections. As illustrated, in one embodiment, the classification technique classifies, in real-time, a "Not Used" state, an "Improper Use" state (that is, "Device being used for other purposes" state, "Improper Stride (insufficient weight dependence)" state, "Improper Stride (incorrect handgrip)" state, and an "Improper Stride (incorrect device orientation)" state) and a "Proper Use (Proper Stride)" state for each user. For example, if a user is classified in a usage state, "Improper Stride (insufficient weight dependence)", then a feedback, in real-time, can be sent to the user to place more weight on the mobility aid device 10.

The threshold values may be determined by collecting data relating to typical usage of the mobility aid device 10 or may be determined by experts. Exemplary threshold values are illustrated in Table-1 shown below.

TABLE 1

|  | Threshold | | |
| --- | --- | --- | --- |
|  | 1 | 2 | 3 |
| $\phi_{thres}$ (°) | 20 | 20 | 20 |
| $\theta_{thres}$ (°) | 30 | 30 | 30 |
| Period of $\omega_x(t)$ (s) | [0.5, 2.1] | [0.5, 2.1] | [0.5, 2.1] |
| $F'_{thres}$ (average, lbs/stride) | 7.1 | 6.3 | 2.0 |
| $F_{thres}$ (maximum, lbs/stride) | 7.1 | 7.1 | 4.0 |
| $\omega_x$ (°/s) | 13.0 | 21.0 | 21.0 |
| Classification Rates (%) | 99.2% | 97.0% | 99.0% |

Figure 7:
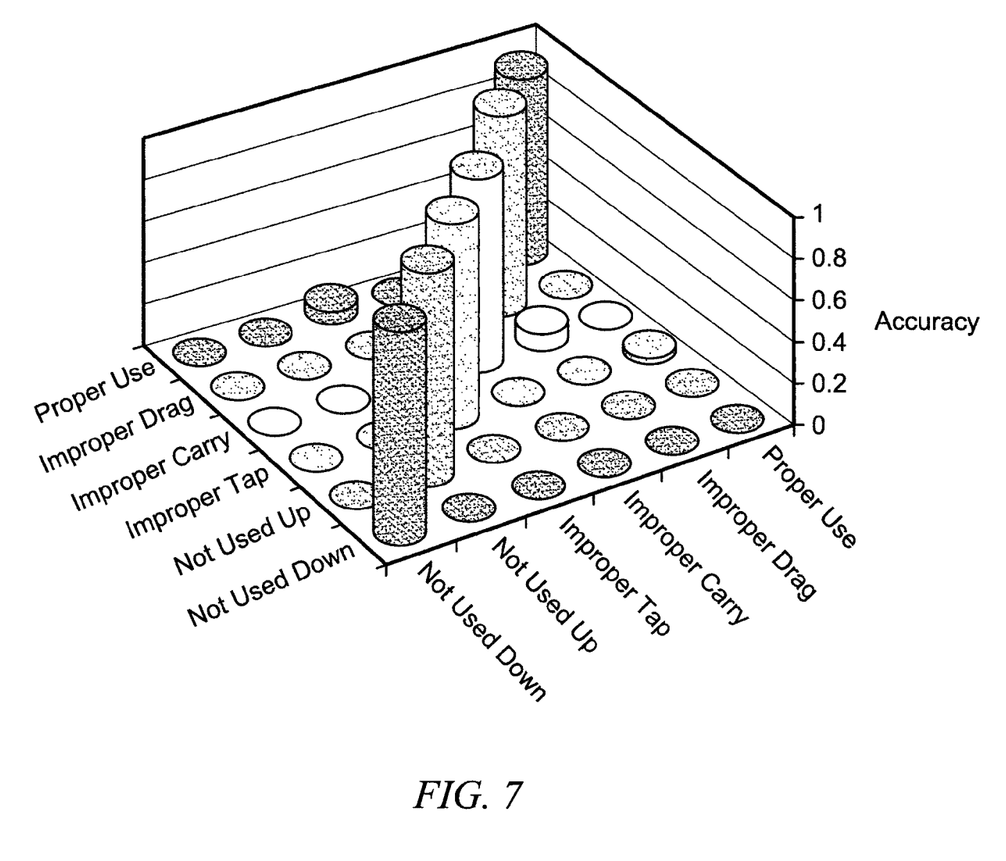
FIG. 7 illustrates a classification matrix that displays an exemplary classification of usage states generated by a typical usage of the mobility aid device shown in FIG. 1, in accordance with one embodiment of the present invention.

In another embodiment, a classification matrix may also be used to represent the various usage states. FIG. 7 illustrates a classification matrix that displays an exemplary classification of usage states generated by a typical usage of the mobility aid device 10, in accordance with one embodiment of the present invention. As illustrated, the states include a "Proper Use" state, an "Improper Use" state ("Improper Drag", "Improper Carry" and "Improper Tap") and a "Not Used" state ("Not Used Up" and "Not Used Down"). These states correspond to states generated or initiated by the usage of the mobility aid device 10.

In certain embodiments, the mobility aid device 10 may also be augmented with wearable sensors. For example, wearable motion sensors can provide additional data about the usage state of a user. In one embodiment, data measurements from body-worn motion sensors, including a tri-axial accelerometer and a single gyroscope are acquired via the Bluetooth interface in the mobility aid device 10 and integrated with the data measurements acquired from the sensors 12, 14, 15 and 16 in the mobility aid device 10. In a particular embodiment, the mobility aid device 10 when augmented with the wearable motion sensors may be used to detect additional usage states, such as, for example, a "Proper Use" state, an "Improper Drag—Limp" state, an "Improper Drag—Walk" state, and "Improper Carry—Limp" state, an "Improper Carry—Walk" state, an "Improper Tap—Arm Extended" state, an "Improper Tap—Arm Not Extended" state, a "Not used up—Standing" state, a "Not used up—Seated" state, a "Not used up—Prone" state, a "Not used down—Standing" state, a "Not used down—Seated" state and a "Not used down—Prone" state.

In certain situations it is desirable to perform accurate identification of usage states based on using a minimum or a reduced number of sensors and reducing the total energy usage in the mobility aid device 10. Accordingly, in yet another embodiment, the sensor processing and inference module 44 or 56 includes a sensor selection technique to determine an optimal combination of sensors that will perform accurate usage state identification while reducing the overall energy consumed by the mobility aid device 10, thereby prolonging the life-cycle of the mobility aid device 10.

In a particular embodiment, the sensor selection technique is based on formulating an energy-aware cost function (optimization function) that computes particular sensor combination alternatives based on suggestions and preferences set forth by users and/or expert domain knowledge of the mobility aid device 10. Specifically, the optimization function guides the suggestion of actions that are recommended to the user or that are accomplished automatically, such as by inserting/removing or turning on/off part-time wearable sensors, or based on the use of a standalone instrument.

In one embodiment, the development of the optimization function comprises (1) the formulation of a decision matrix D that denotes a simple form of expert domain knowledge and user preferences in sensor selection, (2) the calculation of the energy-aware benefit of each action, and (3) the selection of the action that yields the maximum energy-aware benefit.

Equation (7) below illustrates an exemplary decision matrix. In the [m×n] decision matrix D, shown below, the columns correspond to user states, $z_j$, and the rows correspond to a decision in selecting an alternative sensor configuration, $a_i$. The parameters $d_{ij}$ define a relative influence of $z_j$ in choosing $a_i$.

$$D = \begin{array}{c} \\ a_1 \\ \\ a_i \\ \\ a_n \end{array} \begin{pmatrix} z_1 & \cdots & z_j & \cdots & z_m \\ d_{11} & \cdots & d_{1j} & \cdots & d_{1m} \\ \cdots & \cdots & \cdots & \cdots & \cdots \\ d_{i1} & \cdots & d_{ij} & \cdots & d_{im} \\ \cdots & \cdots & \cdots & \cdots & \cdots \\ d_{n1} & \cdots & d_{nj} & \cdots & d_{nm} \end{pmatrix} \quad (7)$$

In the formulation of this decision matrix, expert domain knowledge can narrow down the problem of estimating $d_{ij}$. For example, an expert may determine the use of some sensors to be independent of some user states by assigning zero (0) to $d_{ij}$, indicating that $z_j$ has no influence over $a_i$. The relative values of the non-zero parameters $d_{ij}$ define the user's preferences in choosing one out of a set of n alternatives in the presence of m states. The values are chosen so that the ratio (shown in equation 8) between the expected values of the relevant (non-zero) rows correspond to the user preference threshold $\theta_{i,k}$ in selecting different alternatives $a_i$ and $a_k$. In one embodiment, the selected cost metric corresponds to energy usage. Various combinations of sensors may be defined such that they provide accurate state identification, while optimizing energy usage.

$$\theta_{i,k} = \frac{E(d_{kj})}{E(d_{ij})} \quad (8)$$

The expected energy-aware benefit $EU(a_i)$ of each alternative configuration is calculated by incorporating the user state as shown in equation (9) below:

$$EU(a_i) = \sum_{j=1}^{m} p_j d_{ij} \quad (9)$$

wherein $$p_j = p(C = c_j | F) \geq 0 \text{ and } \sum_{j=1}^{m} p_j = 1$$

is a probability distribution obtained from the Naïve Bayes classifier shown in equation 3. Then, the alternative with the largest expected energy-aware benefit is selected as the optimal sensor configuration as illustrated in equation (10) below:

$$i^* = \text{argmax}_{i=1,\ldots,n} EU(a_i) \quad (10)$$

wherein the function $\text{argmax}_x [f(x)]$ returns an argument x such that the value of the function f(x) is maximized. Observe that each alternative should be optimal in at least one of the user states. Otherwise, the alternative is deemed to be dominated and is removed from the decision matrix.

In one embodiment, the energy-aware alternatives for optimal sensor selection are determined as follows. The Naïve Bayes classifier is incorporated with the utility function in which the alternatives in the decision matrix are A={Device Only, Device+Hip, Device+Arm, Device+Hip+Arm}. The values in the decision matrix D reflect a form of expert domain knowledge and user preferences in selecting the body sensors worn at the hips and arms. The relative values of the numbers determine the optimal set of sensors to be used when a user state with an inference certainty is detected. For example, only the mobility aid device 10 is used when a user state is detected with a certainty higher than 95%. When a user state is uncertain, all the sensors (Device+Hip+Arm) may be activated, and their sensor values integrated with the mobility aid device 10 to determine the usage state.

The disclosed embodiments have several advantages including the ability to accurately detect and classify usage states related to usage of a mobility aid device, perform accurate identification of usage states based on determining an optimal set of sensors that reduce the total energy consumption in the mobility aid device, provide active guidance to a user regarding proper usage of the mobility aid device through real-time feedback mechanisms, prevent improper usage of the mobility aid device that may lead to various falls and injuries, predict possible outcomes such as high risk of falling associated with a user, communicate the risk to a caregiver or a clinician associated with the user and determine a user's preference of locations typically visited by a user and suitability of those locations by analyzing usage patterns associated with the user.

An embodiment of the present invention relates to a computer storage product with a computer-readable medium having computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs, DVDs and holographic devices; magneto-optical media; and hardware devices that are specially configured to store and execute program code, such as application-specific integrated circuits ("ASICs"), programmable logic devices ("PLDs") and ROM and RAM devices. Examples of computer code include machine code, such as produced by a compiler, and files containing higher-level code that are executed by a computer using an interpreter. For example, an embodiment of the invention may be implemented using Java, C++, or other object-oriented programming language and development tools. Another embodiment of the invention may be implemented in hardwired circuitry in place of, or in combination with, machine-executable software instructions.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A non-transitory computer readable storage medium comprising executable instructions to:
    receive sensor data measurements associated with usage of a mobility aid device from a plurality of sensors;
    extract a plurality of sensor feature parameters from the sensor data measurements; and
    based on the sensor feature parameters, classify the usage of the mobility aid device into a usage state classification, wherein the usage state classification is selected from proper use, improper use, and not used;
    wherein the sensor data measurements include angular rate data measurements, force data measurements and linear acceleration data measurements; and
    wherein the executable instructions to classify the usage of the mobility aid device include executable instructions to calculate a plurality of acceleration vectors from the angular rate data measurements, force data measurements and linear acceleration data measurements.

2. The non-transitory computer readable storage medium of claim 1, further comprising executable instructions to provide real-time feedback to a user of the mobility aid device, wherein the real-time feedback includes visual feedback configured for a graphical user interface of a display screen, and wherein the visual feedback provides a graphical representation of the sensor data measurements.

3. The non-transitory computer readable storage medium of claim 2, wherein the executable instructions to provide the real-time feedback include executable instructions to generate an audio tone indicative of the usage state.

4. The non-transitory computer readable storage medium of claim 1, wherein the sensor feature parameters include at least one of a fundamental frequency amplitude parameter and a spectrum energy parameter, extracted based on applying a Fast Fourier Transform to the sensor data measurements.

5. The non-transitory computer readable storage medium of claim 4, wherein the sensor feature parameters further include at least one of a ratio of the fundamental frequency amplitude parameter to the spectrum energy parameter, a mean of a time-series of the sensor data measurements, and a maximum slope of a time-series of the sensor data measurements.

6. The non-transitory computer readable storage medium of claim 1, wherein the executable instructions to classify the usage of the mobility aid device include executable instructions to create sensor feature vectors.

7. The non-transitory computer readable storage medium of claim 1, wherein the executable instructions to classify the usage of the mobility aid device include executable instructions to utilize a Naïve Bayes classifier model.

8. The non-transitory computer readable storage medium of claim 1, wherein the executable instructions to classify the usage of the mobility aid device include executable instructions to utilize a decision tree-based classification technique.

9. The non-transitory computer readable storage medium of claim 1, wherein the executable instructions to extract the sensor feature parameters include executable instructions to extract a swing characteristic from the angular rate data measurements.

10. The non-transitory computer readable storage medium of claim 1, wherein the executable instructions to extract the sensor feature parameters include executable instructions to extract a user's change in direction from the angular rate data measurements.

11. The non-transitory computer readable storage medium of claim 1, wherein the executable instructions to classify the usage include executable instructions to utilize a learning technique.

12. A non-transitory computer readable storage medium, comprising executable instructions to:
receive sensor data measurements associated with usage of a mobility aid device from a plurality of sensors;
extract a plurality of sensor feature parameters from the sensor data measurements; and
based on the sensor feature parameters, classify the usage of the mobility aid device into a usage state classification, wherein the usage state classification is selected from proper use, improper use, and not used;
wherein the executable instructions to classify the usage of the mobility aid device include executable instructions to determine a subset of the plurality of sensors to be used in the mobility aid device, based on an optimal combination of sensors that provides accurate usage state identification and reduced overall energy consumption; and
wherein the subset of the plurality of sensors is derived based on an energy-aware cost function applied to the plurality of sensors, wherein the cost function includes a decision matrix related to a plurality of alternate configurations, and a calculation of an energy-aware benefit for each of the plurality of alternate configurations.

13. The mobility aid device of claim 12, wherein the plurality of sensors comprise at least one of a three-axis accelerometer, a single-axis gyroscope and a pressure sensor.

14. The mobility aid device of claim 13, wherein the plurality of sensors are configured to detect at least one of a downward force, a linear acceleration and an angular rate associated with the usage of the mobility aid device.

15. A mobility aid device comprising:
a plurality of sensors including a three-axis accelerometer, at least one single-axis gyroscope and at least one pressure sensor; and
a computational unit coupled to the plurality of sensors, wherein the computational unit is configured to:
process outputs of the plurality of sensors and detect an applied force, a linear acceleration and an angular rate associated with usage of the mobility aid device;
classify usage of the mobility aid device into a usage state, wherein the usage state is selected from a first group, and members of the first group include proper use, improper use, and not used; and
provide feedback regarding the usage state of the mobility aid device;
wherein the computational unit is further configured to receive data from a wearable sensor, and wherein the data from the wearable sensor allows the computational unit to select the usage state from a second group that is larger than and including the first group.

16. The mobility aid device of claim 15, wherein the computational unit is further configured to generate an audio tone indicative of the usage state.

17. The mobility aid device of claim 15, wherein the computational unit comprises an audio-visual interface module configured to generate an audio output and a visual output of the usage state associated with the mobility aid device, wherein the visual output includes a graphical representation of the sensor data measurements.

18. The mobility aid device of claim 15, wherein the computational unit comprises a sensor processing and inference module configured to extract the sensor feature parameters from the sensor data measurements and derive the usage state corresponding to the usage of the mobility aid device, based on the sensor feature parameters.

19. The mobility aid device of claim 18, wherein the sensor processing and inference module is configured to perform a plurality of feedback cycles associated with the usage of the mobility aid device until proper usage is detected, wherein each of the plurality of feedback cycles includes:
providing a present usage state to a user of the mobility aid device;
extracting sensor feature parameters from sensor data measurements acquired by the selected subset of the plurality of sensors; and
deriving an updated usage state based on the sensor feature parameters.

20. The mobility aid device of claim 15, wherein the computational unit is further configured to deactivate a subset of the plurality of sensors.

21. The mobility aid device of claim 15, wherein the computational unit is configured to utilize a Naïve Bayes classifier model to process the outputs of the plurality of sensors.

* * * * *